(12) United States Patent
Sandburg

(10) Patent No.: US 11,938,264 B2
(45) Date of Patent: Mar. 26, 2024

(54) METHOD FOR REMOVING DEBRIS FROM A VACUUM LINE IN A DENTAL OFFICE

(71) Applicant: Rodney A. Sandburg, Oklahoma City, OK (US)

(72) Inventor: Rodney A. Sandburg, Oklahoma City, OK (US)

( * ) Notice: Subject to any disclaimer, the term of this patent is extended or adjusted under 35 U.S.C. 154(b) by 0 days.

(21) Appl. No.: 17/937,679

(22) Filed: Oct. 3, 2022

(65) Prior Publication Data
US 2023/0025062 A1 Jan. 26, 2023

Related U.S. Application Data

(62) Division of application No. 17/464,054, filed on Sep. 1, 2021, now Pat. No. 11,478,580.
(Continued)

(51) Int. Cl.
*A61M 1/00* (2006.01)
*A61L 2/10* (2006.01)
*B08B 9/032* (2006.01)

(52) U.S. Cl.
CPC ............ *A61M 1/79* (2021.05); *A61L 2/10* (2013.01); *B08B 9/0323* (2013.01); *B08B 9/0325* (2013.01); *A61L 2202/11* (2013.01); *A61L 2202/15* (2013.01); *A61L 2202/17* (2013.01); *B08B 2209/032* (2013.01)

(58) Field of Classification Search
CPC ....... B08B 9/027; B08B 9/032; B08B 9/0323; B08B 2209/032; A61C 17/135
See application file for complete search history.

(56) References Cited

U.S. PATENT DOCUMENTS 2,639,600 A 5/1953 Abresch
4,877,043 A 10/1989 Carmichael et al.
(Continued)

FOREIGN PATENT DOCUMENTS

CN 208974791 U 6/2019
DE 3900108 A1 7/1990
(Continued)

OTHER PUBLICATIONS

Machine translation: JPH09173359; Hanabusa, S. (Year: 1997).*
(Continued)

*Primary Examiner* — Natasha N Campbell
(74) *Attorney, Agent, or Firm* — DUNLAP CODDING, P.C.

(57) ABSTRACT

Systems and methods are described to flush debris from a suction pipe network installed in a medical office. A filter, an amalgam separator and at least one flexible vacuum line are disconnected from a suction pipe network. The suction pipe network has a main trunk line, a downstream end, and at least one branch line. A neutral pH cleaning fluid solution is passed through the main trunk line from a location downstream of the at least one branch line to flush debris from the main trunk and the at least one branch line. The neutral pH cleaning fluid solution is collected subsequent to the neutral pH cleaning fluid solution being circulated through the main trunk line and the at least one branch line. Then, the filter, the amalgam separator and the at least one flexible vacuum line are reconnected to the suction pipe network.

5 Claims, 10 Drawing Sheets

Related U.S. Application Data

(60) Provisional application No. 63/073,162, filed on Sep. 1, 2020.

(56) References Cited

U.S. PATENT DOCUMENTS

| | | |
|---|---|---|
| 5,554,228 A | 9/1996 | Giordano et al. |
| 6,482,370 B2 | 11/2002 | Holsclaw et al. |
| 6,550,487 B1 | 4/2003 | Duckett et al. |
| 10,272,479 B2 | 4/2019 | Pickett |
| 2003/0036033 A1 | 2/2003 | Chandler |
| 2005/0187528 A1 | 8/2005 | Berg |
| 2005/0199535 A1* | 9/2005 | Yates .................. A61C 17/065 210/104 |
| 2005/0239016 A1 | 10/2005 | McCary |
| 2017/0120304 A1 | 5/2017 | Schaer |

FOREIGN PATENT DOCUMENTS

| | | |
|---|---|---|
| JP | H0698158 B2 | 12/1994 |
| JP | 09173359 A * | 7/1997 |
| JP | 2017006214 A | 1/2017 |
| KR | 2017126118 A | 11/2017 |
| WO | WO 2008062104 A1 | 5/2008 |

OTHER PUBLICATIONS

Machine Translation: JPH0698158; Tanaka et al. (Year: 1994).
Machine Translation: JP 2017006214; Fujisawa et al. (Year: 2017).
Machine Translation; KR 2017126118; Kim, S. (Year: 2017).
Machine Translation: CN208974791U; Xilong (Year: 2019).
Machine Translatio: DE3900108; Panzer et al. (Year: 1990).

* cited by examiner

METHOD FOR REMOVING DEBRIS FROM A VACUUM LINE IN A DENTAL OFFICE

CROSS-REFERENCE TO RELATED APPLICATIONS

This application is a divisional of U.S. Ser. No. 17/464,054, filed on Sep. 1, 2021, and claims priority to the provisional patent application identified by U.S. Ser. No. 63/073,162 filed on Sep. 1, 2020, the entire contents of all of which are hereby incorporated herein by reference in their entirety.

BACKGROUND

In the practice of dentistry, many procedures require the evacuation of saliva, blood, tissue, bodily fluids, and other debris from the oral cavity of patients. Dental offices commonly rely on power suction systems to provide suction necessary to evacuate such debris. These power suction systems are typically located in operatories or exam rooms and are connected by a network of suction pipes, either underground or overhead, that lead to a centrally located suction unit. The suction unit generally consists of a powerful vacuum-type unit located centrally in an office and, often, near a drain. Typically, these vacuum-type units are also connected to a central filter and/or amalgam separator. Large debris evacuated from the oral cavity of a patient is typically collected in baskets and filters in each exam room. Smaller debris travels through the suction lines and are typically collected in filters at or near the suction unit.

As the debris and fluids are transferred through the system of pipes, particulate and sediment settle within the pipe and collect at the base, bends, and other areas of the pipes. Additionally, because the pipes are continually moist or wet, biofilm forms within the walls of the pipe. The sediment and biofilm collect over time and may constrict, impede, or interrupt the free flow of debris through the pipes. To clean the pipes, practitioners typically rely on the existing power suction equipment to introduce various solutions into the pipes to break down the sediment and biofilm.

Such cleaning methods include introducing enzyme solutions into the pipes using existing power suction systems. Although enzyme solutions may dissolve biological solids, i.e., biofilm within the pipes, enzyme solutions have minimal or no effect on other non-biological solids that accumulate in the pipes. In the past, acid solutions have also been introduced into the pipes through existing power suction systems in an attempt to dissolve non-biological solids that collect within the pipes. However, the use of acid solutions may cause dissolved solids to release mercury vapors into the air and into city sewer systems, as well as void any warranty on office amalgam separators. As such, the use of acid solutions to clean dental vacuum lines is no longer an accepted practice within the industry.

Therefore, a need exists for a system and method of removing both biological and non-biological debris that accumulate in dental pipe systems that do not require the use of corrosive solutions. It is such a system and method that the presently disclosed inventive concepts are directed.

SUMMARY

A system and method for removing debris from pipes of a suction pipe network in a medical office are disclosed. The medical office will be described herein by way of example as a dental office. It should be understood, however, the present disclosure is not limited to only a dental office. The problem of removing biological and non-biological debris without the use of a corrosive solution is addressed by relying on turbulent flow created by a pump to effect cleaning of the pipes using a cleaning fluid solution having a neutral pH. Furthermore, the problem of voiding the warranty on an office amalgam separator and/or filter is avoided by decoupling the suction pipe network from the office amalgam separator and/or filter, and instead using a separate filter system to remove debris from the cleaning fluid solution that is circulated throughout the pipes of the suction pipe network. The cleaning of the suction pipe network may be achieved by utilizing a vacuum line cleaning system. To remove debris from pipes of the suction pipe network, the suction pipe network may be decoupled from all existing lines, filters, hoses, dental instruments, etc. The suction pipe network may also be decoupled from a central vacuum-like unit, amalgam separator and/or filter, and also from any power suction system present in each examination room or operatory. The vacuum line cleaning system may be rolled into the dental office and placed in a central location with access to the suction pipe network. The vacuum line cleaning system includes a pump to circulate a cleaning fluid solution through at least a portion of the pipes of the suction pipe network to effect cleaning of at least a portion of the suction pipe network. The pump may be fluidly connected to the suction pipe network at the location from which the central vacuum-like unit was decoupled. The vacuum line cleaning system also includes at least one filter, that is connected to the suction pipe network. Upon circulation of the cleaning fluid solution by the pump, the filter receives the cleaning fluid solution that has been circulated through the suction pipe network and removes debris therefrom. In some embodiments, multiple filters are provided, and may be fluidly connected to the suction pipe network at each examination room or operatory. The vacuum line cleaning system may also be provided with a holding tank having a holding chamber storing the cleaning fluid solution. The pump is in fluid communication with the holding chamber, and pumps the cleaning fluid solution throughout at least a portion of the suction pipe network. In some embodiments, the suction pipe network includes a main trunk link formed by one or more of the pipes. In these embodiments, the cleaning fluid solution may flow through the main trunk line of the suction pipe network and into each of the exam room(s) through pipes forming branch lines that extend from the main trunk line. From the branch line of each exam room the cleaning fluid solution is passed through the filter to remove any debris that was collected by the cleaning fluid solution from the suction pipe network. After being filtered, the cleaning fluid solution may be returned into the holding chamber to be recirculated through the suction pipe network or stored in a collection tank. After a sufficient time to remove the debris from within the pipes of the suction pipe network, the pump may be reversed to evacuate at least a portion of the pipes of the suction pipe network of any remaining cleaning fluid solution.

Consistent with an aspect of the present disclosure, the vacuum line cleaning system may comprise a cart having a support surface; a holding tank positioned on the support surface, the holding tank having a holding chamber adapted to contain a cleaning fluid solution having a neutral pH. The holding tank has a chamber outlet and a chamber inlet, the chamber outlet and the chamber inlet configured to provide fluid access to the holding chamber. The cart includes a plurality of wheels supporting the support surface such that the support surface can be moved by rolling the wheels across a surface without tipping the holding tank. The vacuum line cleaning system also includes a suction pipe network installed in a medical office. The suction pipe network may comprise a plurality of pipes connected to form a main trunk line and at least one branch line extending from the main trunk line. In the embodiments including a main trunk line, the main trunk line has a downstream end. The vacuum line cleaning system includes at least one filter having a filter inlet and a filter outlet, the filter inlet in fluid communication with the at least one branch line. The cart supports a pump having a first port and a second port. The first port is in fluid communication with the holding chamber outlet and the second port is in fluid communication with the downstream end of the main trunk line, the pump is selectively operable for flow from the first port to the second port in a first direction to circulate the cleaning fluid solution through the main trunk line, and from the second port to the first port in a second direction to evacuate the cleaning fluid solution from the main trunk line.

BRIEF DESCRIPTION OF THE DRAWINGS

The accompanying drawings, which are incorporated in and constitute a part of this specification, illustrate one or more implementations described herein and, together with the description, explain these implementations. The drawings are not intended to be drawn to scale, and certain features and certain views of the figures may be shown exaggerated, to scale or in schematic in the interest of clarity and conciseness. Not every component may be labeled in every drawing. Like reference numerals in the figures may represent and refer to the same or similar element or function. In the drawings.

DETAILED DESCRIPTION

Figure 1:
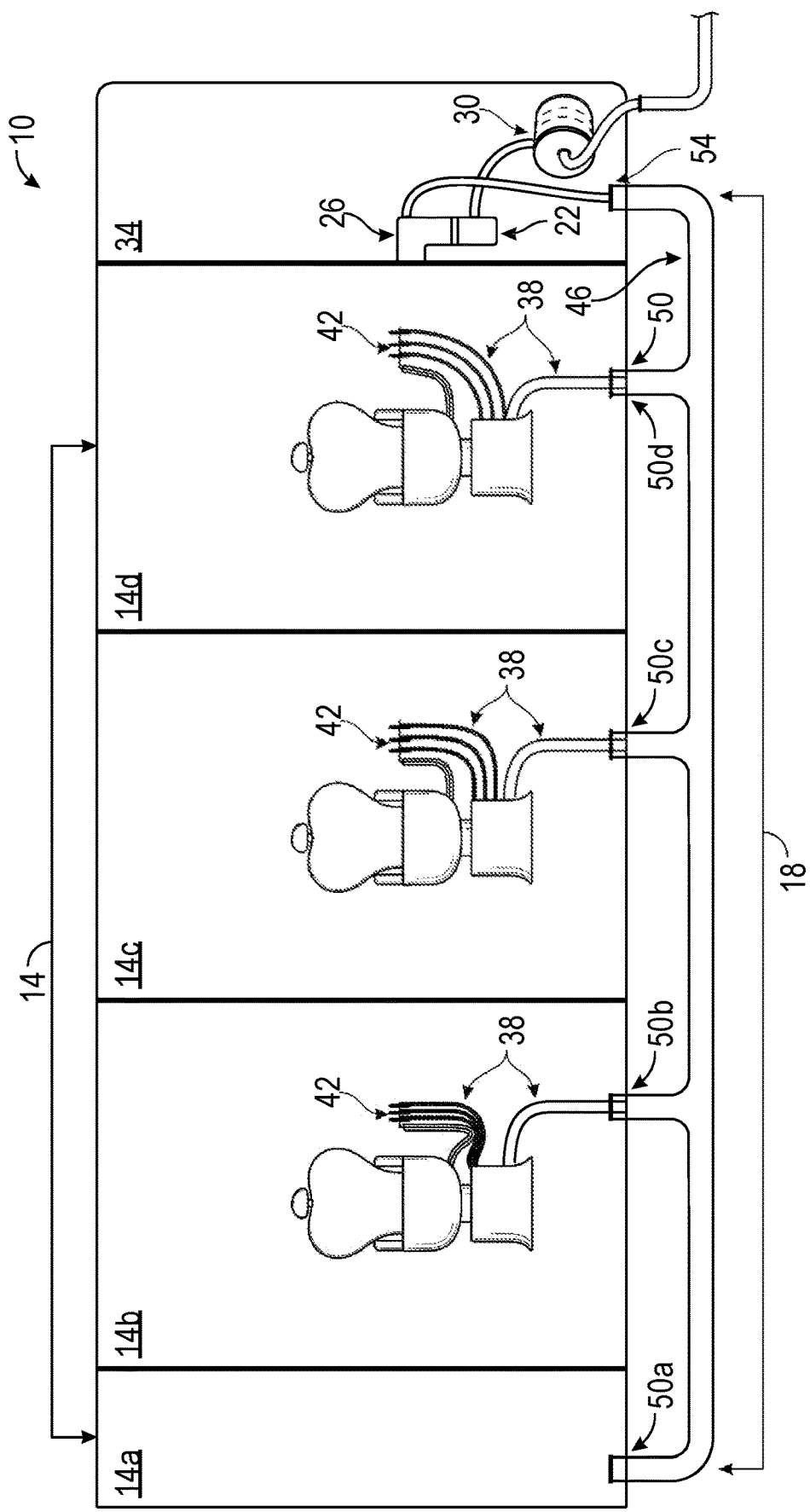
FIG. 1 is an illustration of an exemplary layout of a dental office having a suction pipe network connected to an office amalgam separator, filter, and suction unit.

The following detailed description refers to the accompanying drawings. The same reference numbers in different drawings may identify the same or similar elements.

Before explaining at least one embodiment of the inventive concept disclosed herein in detail, it is to be understood that the inventive concept is not limited in its application to the details of construction and the arrangement of the components or steps or methodologies set forth in the following description or illustrated in the drawings. The inventive concept disclosed herein is capable of other embodiments or of being practiced or carried out in various ways. Also, it is to be understood that the phraseology and terminology employed herein is for the purpose of description and should not be regarded as limiting in any way.

In the following detailed description of embodiments of the inventive concept, numerous specific details are set forth in order to provide a more thorough understanding of the inventive concept. It will be apparent to one of ordinary skill in the art, however, that the inventive concept within the disclosure may be practiced without these specific details. In other instances, well-known features have not been described in detail to avoid unnecessarily complicating the instant disclosure.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or more and the singular also includes the plural unless it is obvious that it is meant otherwise.

Further, use of the term "plurality" is meant to convey "more than one" unless expressly stated to the contrary.

As used herein, qualifiers like "substantially," "about," "approximately," and combinations and variations thereof, are intended to include not only the exact amount or value that they qualify, but also some slight deviations therefrom, which may be due to manufacturing tolerances, measurement error, wear and tear, stresses exerted on various parts, and combinations thereof, for example.

The use of the term "at least one" or "one or more" will be understood to include one as well as any quantity more than one. In addition, the use of the phrase "at least one of X, V, and Z" will be understood to include X alone, V alone, and Z alone, as well as any combination of X, V, and Z.

The use of ordinal number terminology (i.e., "first", "second", "third", "fourth", etc.) is solely for the purpose of differentiating between two or more items and, unless explicitly stated otherwise, is not meant to imply any sequence or order or importance to one item over another or any order of addition.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As discussed above, there exists a need for a system and method that removes biological and non-biological debris from a suction pipe network installed in a medical office. The prior art addressed the removal of biological debris, but not the removal of non-biological debris using a non-corrosive cleaning solution, for example, a cleaning solution having a neutral pH. Moreover, the prior art addressed the cleaning of suction pipe networks by utilizing existing vacuum units, but not a separate system. The present disclosure addresses these deficiencies with a methodology for cleaning suction pipe networks installed in medical offices by utilizing turbulent flow created by a separate pumping unit circulating a non-corrosive cleaning solution through the suction pipe network.

Referring now to FIG. 1, shown therein is a diagram illustrating a configuration of an exemplary dental office 10. As shown in FIG. 1, the dental office 10 has a plurality of examination rooms 14. By way of example, four examination rooms 14 are shown in FIG. 1 and designated by the reference numerals 14a, 14b, 14c and 14d. The dental office 10 is also provided with a suction pipe network 18, an amalgam separator 22, a central filter 26, a central suction unit 30, and an equipment room 34, a plurality of flexible vacuum lines 38, and dental instruments 42. The suction pipe network 18 extends from the equipment room 34 to each of the examination rooms 14. The amalgam separator 22, the central filter 26, and the central suction unit 30 may be located within the equipment room 34. The central filter 26 is connected to the suction pipe network 18. The amalgam separator 22 is fluidly connected to the central filter 26 and operates to filter debris before it reaches the central filter 26. The central suction unit 30 is fluidly connected to the central filter 26, and serves to draw fluid through the suction pipe network 18, the amalgam separator 22, and the central filter 26. The dental instruments 42 are positioned within the examination rooms 14. The dental instruments 42 are connected to the flexible vacuum lines 38, which are connected to the suction pipe network 18. In other words, the flexible vacuum lines 38 fluidly connect the suction pipe network 18 to respective dental instruments 42. The suction pipe network 18 includes a plurality of pipes forming a main trunk line 46 and at least one branch line 50 extending from the main trunk line 46. By way of example, four branch lines 50 are shown in FIG. 1 and designated by the reference numerals 50a, 50b, 50c, and 50d. Each of the at least one branch lines 50 may be located within each of the examination rooms 14. The flexible vacuum lines 38 are fluidly connected to the suction pipe network 18 via the at least one branch line 50. The main trunk line 46 has a downstream end 54 and such downstream end 54 may be located in equipment room 34, as shown in FIG. 1. The central filter 26 is fluidly connected to the suction pipe network 18 via downstream end 54.

During regular operation, for example, a dental practitioner may attend to a patient in one of the examination rooms 14, and may utilize dental instruments 42 to perform dental procedures, such as evacuating debris from a patient's oral cavity. The central suction unit 30 is configured to provide suction to the dental instruments 42 which are in communication with the central suction unit 30 via the suction pipe network 18 through flexible vacuum lines 38. Debris, particulates, and fluids evacuated from a patient's oral cavity by the dental instruments 42 may be transported through the flexible vacuum lines 38, suction pipe network 18 and to the amalgam separator 22 where any large debris is separated before being filtered by the central filter 26. During this process, biological and non-biological debris evacuated from a patient's oral cavity may accumulate and settle in various portions of the suction pipe network 18. The accumulated debris in the suction pipe network 18 may be cleaned using a vacuum line cleaning system 60. The vacuum line cleaning system 60 is discussed in more detail below.

Figure 2:
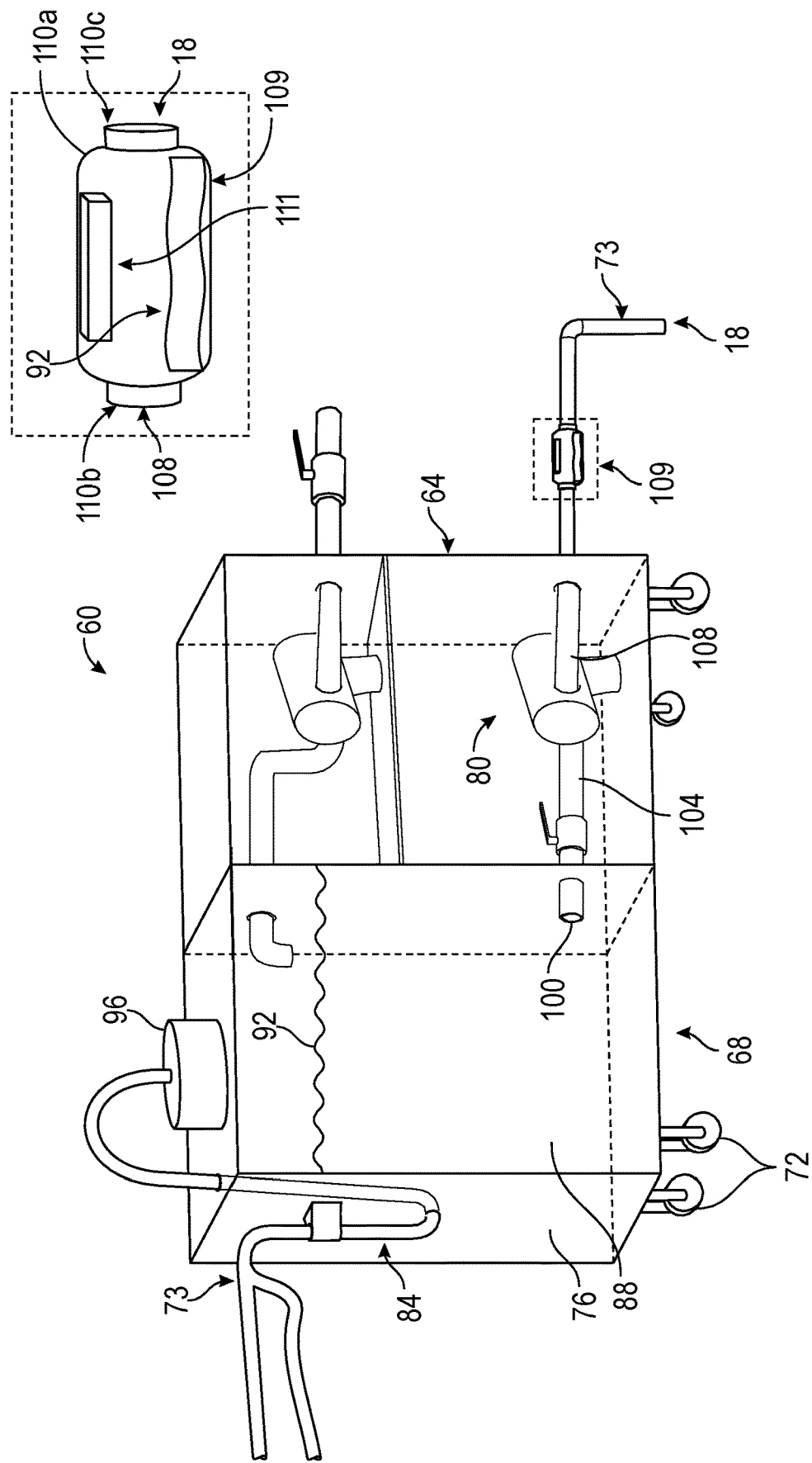
FIG. 2 is a side perspective view of an exemplary embodiment of a system for removing debris from a suction pipe network in a dental office in accordance with the present disclosure.

Referring now to FIG. 2, shown therein is an exemplary embodiment of a vacuum line cleaning system 60 according to the instant disclosure. As shown in FIG. 2, the vacuum line cleaning system 60 is provided with a cart 64 having a support surface 68 and a plurality of wheels 72. The cart 64 may be supported by the plurality of wheels 72 such that the cart 64 can be rolled across a flat surface without tipping. The vacuum line cleaning system 60 may be transported into the dental office 10, and then located in any location within the dental office 10, including, for example, the equipment room 34, or one of the examination rooms 14. The vacuum line cleaning system 60 is also provided with a holding tank 76, a pump 80, and a filter 84. By way of example, the holding tank 76 may be positioned upon support surface 68, as shown in FIG. 2. Holding tank 76 is fluidly connected to the pump 80. The pump 80 is fluidly connected to at least a portion of the suction pipe network 18, e.g., at the downstream end 54 thereof or to one of the branch lines 50, so as to be capable of pumping the contents of holding tank 76 throughout at least a portion of the suction pipe network 18. The filter 84 is fluidly connected to the suction pipe network 18 and the holding tank 76, and serves to remove any debris or particles suspended in the fluid removed from the suction pipe network 18. Flexible piping 73 and hoses may be used to fluidly connect the holding tank 76, the pump 80, the filter 84, and the suction pipe network 18. For example, the pump 80 may be fluidly connected to the downstream end 54 via a flexible piping, and the filter 84 may be fluidly connected to the branch lines 50a, 50b, 50c, and 50d via flexible piping 73. Holding tank 76 has a holding chamber 88 adapted to contain a cleaning fluid solution 92, and a chamber inlet 96 and a chamber outlet 100. Both the chamber inlet 96 and the chamber outlet 100 are configured to provide fluid access to the holding chamber 88. The holding tank 76 may be of any shape or size sufficient to contain sufficient cleaning fluid solution 92 to flush the suction pipe network 18. The cleaning fluid solution 92 may have a neutral pH, for example, a pH of approximately 6 to 8, such that suction pipe network 18 may be cleaned without being subject to corrosive effects. In one embodiment, the neutral pH of the cleaning fluid solution 92 may be approximately 7.9. The cleaning fluid solution 92, for example, may be a non-foaming detergent, a sanitization solution, an enzyme solution, water, air, gasses, UV activated disinfecting solution, or a combination thereof.

In one embodiment, the holding chamber 88 may contain a concentrated cleaning fluid solution 92. The holding chamber 88 may receive a volume of water from an on-site water supply via the chamber inlet 96 to dilute the concentrated cleaning fluid solution 92 to a specified concentration before the cleaning fluid solution 92 is circulated through the suction pipe network 18.

Figure 2A:
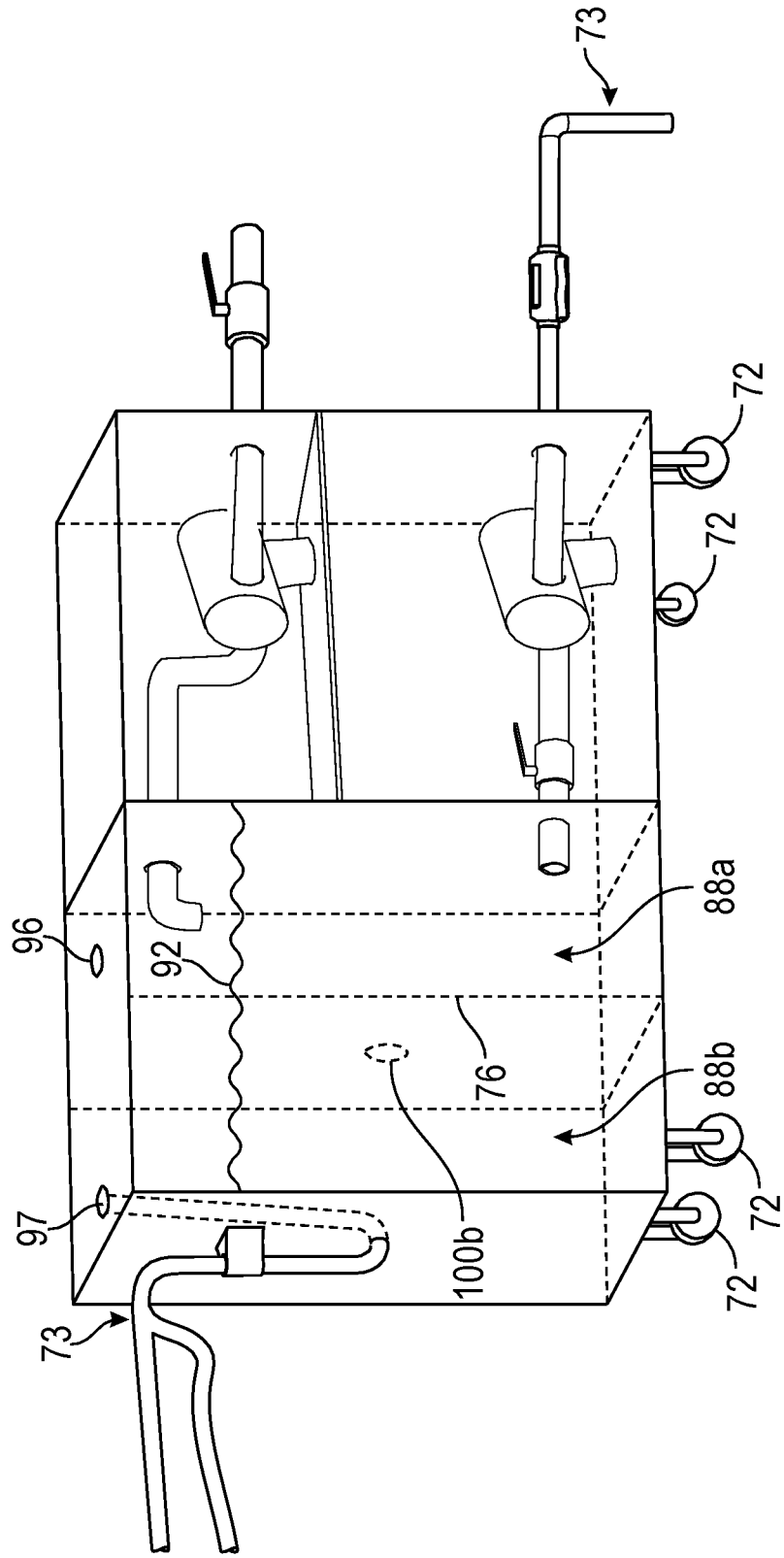
FIG. 2A is a side perspective view of an alternative exemplary embodiment of the system for removing debris from the suction pipe network having a holding tank with more than one holding chamber.

In another embodiment, as shown in FIG. 2A, the holding chamber 88 may be a first holding chamber 88a and the holding tank 76 may further comprise a second holding chamber 88b adapted to contain cleaning fluid solution 92, and a second chamber outlet 100b and a second chamber inlet 97. The second chamber outlet 100b may be in fluid communication with the first holding chamber 88a and the second chamber inlet 97 may be configured to provide fluid access to the second holding chamber 88b. In one embodiment, the first holding chamber 88a may contain a concentrated cleaning fluid solution 92 and the second holding chamber 88b may contain a volume of water. The first holding chamber 88a may receive the volume of water from the second holding chamber 88b via the second chamber outlet 100b so that the concentrated cleaning fluid solution 92 may be diluted to a specified concentration before the cleaning fluid solution 92 is circulated throughout the suction pipe network 18.

The pump 80 has a first port 104 and a second port 108. The first port 104 of the pump may be in fluid communication with the holding chamber 88 via chamber outlet 100 such that the pump 80 may pump cleaning fluid solution 92 out of the holding chamber 88. The second port 108 of the pump 80 may be in fluid communication with the suction pipe network 18 via the downstream end 54 of the main trunk line 46 so that the cleaning fluid solution 92 from the holding chamber 88 may be introduced into the suction pipe network 18. The pump 80 may be selectively operable for flow from the first port 104 to the second port 108 in a first direction, and from the second port 108 to the first port 104 in a second direction. For example, the pump 80 may be operable for flow in the first direction to flush the suction pipe network 18 with the cleaning fluid solution 92, and in the second direction to evacuate the suction pipe network 18 of any remaining cleaning fluid solution 92. The pump 80 may also be operable to alternate between flow in the first direction and the second direction in rapid succession to create a pulsating flow to aid in the removal of debris from the suction pipe network 18. The pump 80 may be connected to and supported by the support surface 68 of the cart 64. In some embodiments, the pump 80 may be located within the cart 64, as shown in FIG. 2. In other embodiments, the pump 80 may be separate from the cart 64, and/or located at a different location within the dental office. The vacuum line cleaning system 60 may include more than one pump 80 and more than one cart 64. The pump may have any suitable max flow rate, such as, for example, a max flow rate of 29 gallons per minute.

In one embodiment, the pump 80 may be configured to circulate cleaning fluid solution 92 through the suction pipe network 18 in a first direction when the first port 104 is in fluid communication with the holding chamber 88 via the chamber outlet 100 and the second port 108 is in fluid communication with the suction pipe network 18 via the downstream end 54. Cleaning fluid solution 92 is pumped out of the holding chamber 88 via the chamber outlet 100 to the first port 104, and from the first port 104 the cleaning fluid solution 92 flows to the second port 108 and into the suction pipe network 18 via the downstream end 54 of the main trunk line 46. The cleaning fluid solution 92 flows through the main trunk line 46, the branch lines 50 and back to the at least one filter 84 via flexible piping 73. In that embodiment, the pump 80 is further configured to evacuate cleaning fluid solution 92 from the suction pipe network 18 when the pump 80 is selectively operated in a second direction opposite from the first direction, where the pump 80 is operable for flow from the second port 108 to the first port 104.

In another embodiment, a ultra violet (UV) disinfection chamber 109 may be interposed between the second port 108 and the suction pipe network 18. The UV disinfection chamber 109 may comprise a housing 110a, the housing 110a having a first end 110b and a second end 110c, wherein the first end 110b is in fluid communication with the second port 108 and the second end 110c is in fluid communication with the suction pipe network 18. The UV disinfection chamber 109 may further comprise at least one ultra violet (UV) light source 111 positioned within the housing 110a, the at least one UV light source 111 may be configured to emit UV light such that the UV light irradiates the cleaning fluid solution 92 as it flows through the housing 110a from the second port 108 prior to entering into the suction pipe network 18. In this embodiment, for example, the cleaning fluid solution 92 may be of a type that is activated by UV light. In another embodiment, the UV disinfection chamber 109 may be interposed between the chamber outlet 100 and the first pump inlet 104 (not shown). In that embodiment, the at least one UV light source 111 may be configured to emit UV light such that the UV light irradiates the cleaning fluid solution 92 as it flows through the housing 110a from the chamber outlet 100 and into the first pump inlet 104.

Figure 2B:
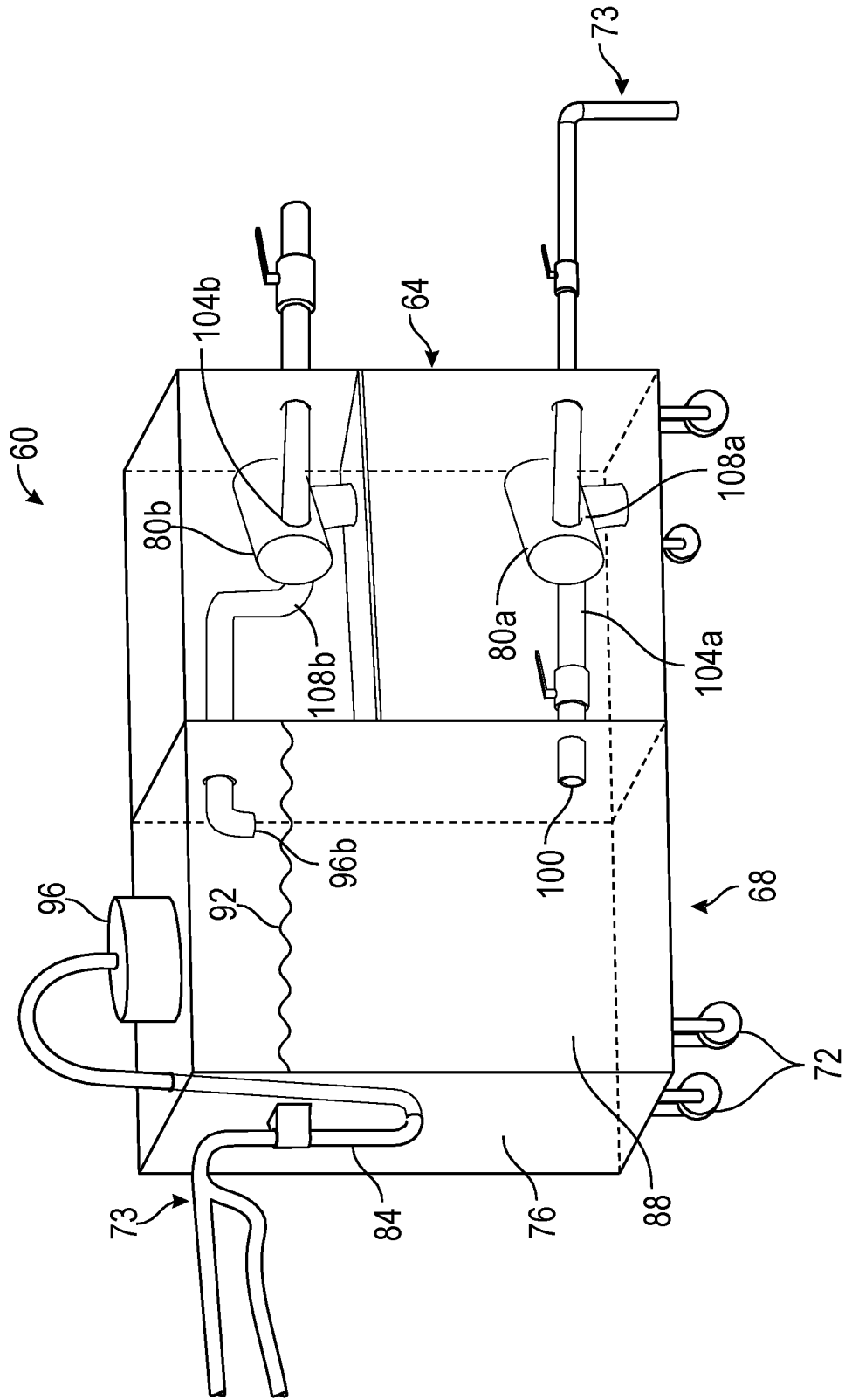
FIG. 2B is a side perspective view of an alternative exemplary embodiment of the system for removing debris from the suction pipe network having more than one pump.

In another embodiment, as shown in FIG. 2B, the pump 80 may be a first pump 80a having a first pump inlet 104a and a first pump outlet 108a. The first pump inlet 104a may be configured to be fluidly connected to the chamber outlet 100, and the first pump outlet 108a may be operable to be fluidly connected to the downstream end 54 of the main trunk line 46. In that embodiment, the vacuum line cleaning system 60 further comprises a second pump 80b, the second pump 80b having a second pump inlet 104b and a second pump outlet 108b. Further, in that embodiment, the holding tank 76 further comprises a chamber pump inlet 96b configured to provide fluid access to the holding chamber 88. The second pump outlet 108b is configured to be connected to the chamber pump inlet 96b, the second pump inlet 104b operable to be connected to the downstream end 54 of the main trunk line 46. Cleaning fluid solution 92 may be circulated in a first direction through the suction pipe network 18 when the downstream end 54 is fluidly connected to the first pump outlet 108a, and the cleaning fluid solution 92 may be circulated in a second direction through the suction pipe network 18 opposite from the first direction when the downstream end 54 is fluidly connected to the second pump inlet 104b.

Figure 3:
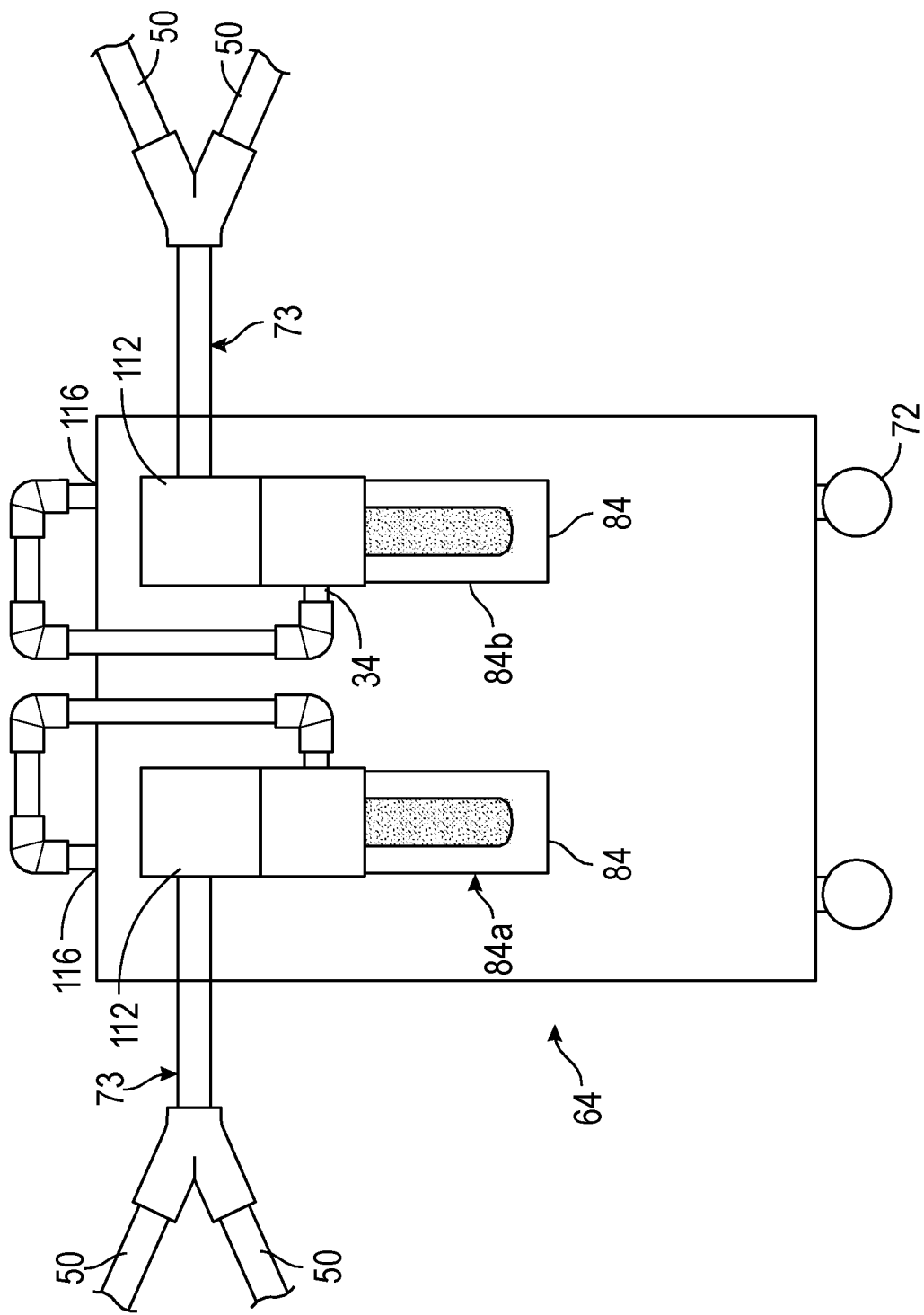
FIG. 3 is a rear perspective view of the exemplary embodiment of FIG. 2.

Referring now to the FIG. 3, shown therein is a rear perspective view of the exemplary embodiment of the vacuum line cleaning system 60 according to the instant disclosure. The vacuum line cleaning system 60 includes the at least one filter 84. By way of example, two filters are shown in FIG. 3. and designated by the reference numerals 84a and 84b. Each of the filters has a filter inlet 112 and a filter outlet 116. The filter inlet 112 may be fluidly connected to the suction pipe network 18 via the at least one branch line 50 so as to permit the debris and particles suspended in the cleaning fluid solution 92 that is removed from the suction pipe network 18 to be filtered via the filter 84. As shown in FIG. 3, the filter inlet 112 may intake cleaning fluid solution 92 from more than one of the at least one branch line 50, for example, by way of a splitter valve. The filter outlet 116 may be fluidly connected to the holding tank 76 via the chamber inlet 96 such that the filtered cleaning fluid solution 92 may be reintroduced into the holding chamber 88 for recirculation after being filtered by the filter 84. The filter 84 may, for example, be mounted to the exterior of the cart 64 as shown in FIG. 3. The filter 84 may also be located in a location different than the cart 64. The filter 84 may be a passive gravity filter. In some embodiments, the filter 84 may be a system of flow through filters with filtration capabilities, for example, of 20, 15, 5, and 1 micron. The filter may also include a separator, such as, for example, a centrifugal separator to separate large debris suspended in the cleaning fluid solution prior to being filtered.

Figure 4:
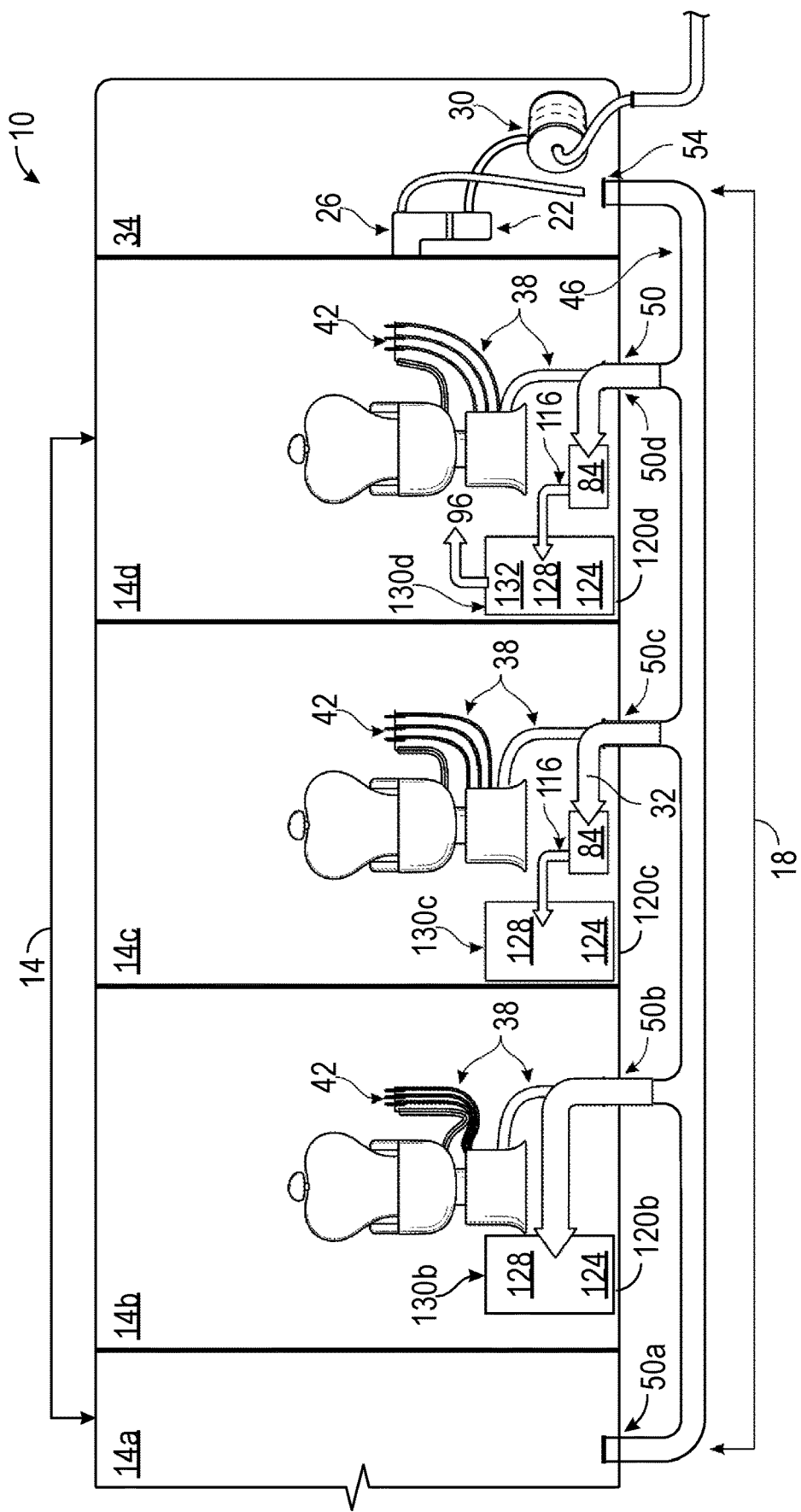
FIG. 4 is a diagrammatic view of an alternative exemplary embodiment of the system for removing debris from the suction pipe network having a plurality of collection tanks placed in respective examination rooms or operatories in accordance with the present disclosure.

As shown in FIG. 4, in one alternative embodiment, the vacuum line cleaning system 60 may further include at least one collection cart 130. By way of example, three collection carts are shown to be located in the dental office 10 in FIG. 4 and designated by the reference numerals 130b, 130c, 130d. The at least one collection cart 130 may be supported by a plurality of wheels which allow the at least one collection cart 130 to be rolled across a flat surface without tipping. Each of the collection carts 130 may also have a collection tank 120, and the collection tank 120 may further include a collection chamber 124 adapted to contain at least a portion of the cleaning fluid solution 92. The collection tanks 120 may be of any shape or size sufficient to contain at least a portion of the cleaning fluid solution 92. The collection tanks 120 may be positioned and supported by the collection cart 130. The collection tank 120 may also be positioned on the support surface 68 of the cart 64 or may be positioned at a location different than the holding tank 76. For example, the collection carts 130b-130d may be located in the examination rooms 14, as shown in FIG. 4. The collection tank 120 may include a collection chamber inlet 128 and a collection chamber outlet 132 to provide access to the collection chamber 124. The collection chamber inlet 128 and collection chamber outlet 132 are configured to provide fluid access to the collection chamber 124. The collection chamber inlet 128 may be in fluid communication with the filter outlet 116 or the at least one branch line 50 and the collection chamber outlet 132 may be in selectable fluid communication with the chamber inlet 96 of the holding chamber 88.

In one embodiment, the collection cart 130 may be positioned in an examination room 14, such as examination room 14d as shown in FIG. 4. In that embodiment, the collection tank 120d may have the collection chamber 124 in fluid communication with the filter outlet 116 and a collection chamber outlet 132 in fluid communication with the chamber inlet 96 of the holding chamber 88 such that cleaning fluid solution 92 may be circulated throughout the suction pipe network 18 and filtered by the filter 84 before being introduced into the collection chamber 124 via the filter outlet 116 prior to being introduced into the holding chamber 88 via the chamber inlet 96 through the collection chamber outlet 132, at which time the cleaning fluid solution 92 may be recirculated. In this embodiment, the central filter 26, amalgam separator 22, and central filter 26 is decoupled from the suction pipe network 18, and the vacuum line cleaning system 60 is coupled to the suction pipe network 18.

Still referring to FIG. 4, in another embodiment, the collection cart 130c may be positioned in an examination room, such as examination room 14c as shown in FIG. 4. In that embodiment, the collection cart 130c may have a collection tank 120 (shown by way of example as collection tanks 120b, 120c and 120d), the collection tank 120 having a collection chamber 124 in fluid communication with the filter outlet 116 via collection chamber inlet 128 such that cleaning fluid solution 92 may be circulated throughout the suction pipe network 18 and filtered by the filter 84 before being introduced into the collection chamber 124 via the filter outlet 116 and collection chamber inlet 128 and where the cleaning fluid solution 92 remains for the remainder of the cleaning process before being collected.

In another embodiment, as shown in FIG. 4, the collection cart 130b may be positioned in an examination room, such as examination room 14b as shown in FIG. 4. In that embodiment, the collection cart 130b may have the collection tank 120, the collection tank 120 having a collection chamber 124 in fluid communication with the at least one branch line 50 of the suction pipe network 18 such that cleaning fluid solution 92 may be circulated throughout at least a portion of the suction pipe network 18 before being introduced into the collection chamber 124 via the collection chamber inlet 128 and where the cleaning fluid solution 92 may remain for the remainder of the cleaning process before being collected for off-site filtration. In some embodiments, each of the branch lines 50a, 50b, 50c and 50d (i.e., a portion of the suction pipe network 18) may be cleaned separated or in combination by passing the cleaning fluid solution 32 through the main trunk line 46 and one or more selected branch lines 50a, 50b, 50c, and 50d, for example.

Figure 5:
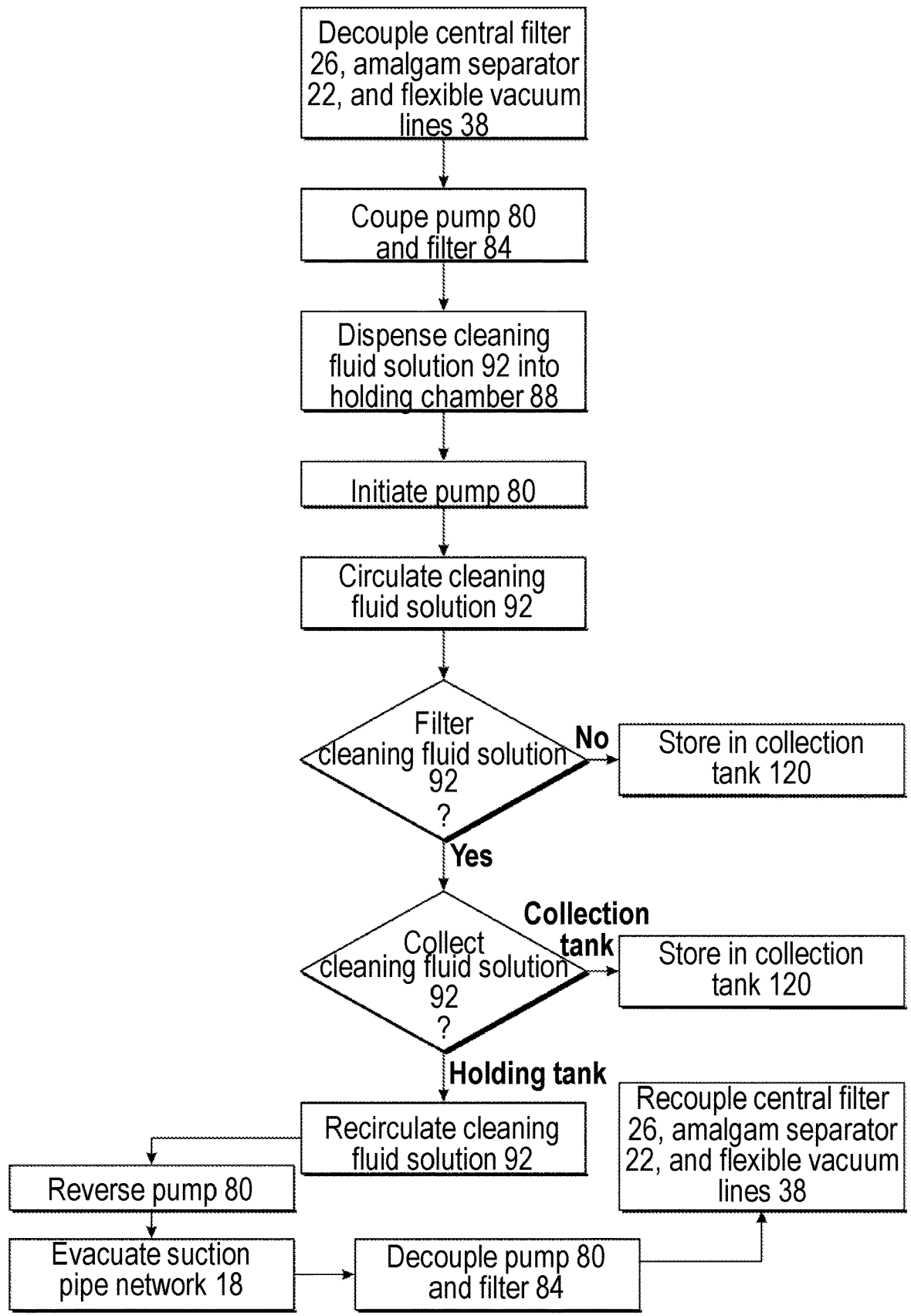
FIG. 5 is a flowchart depicting a methodology for removing debris from a suction pipe network in the dental office in accordance with the present disclosure.

Referring now to FIG. 5, shown therein is a flowchart depicting an exemplary methodology for removing debris from a vacuum line in a dental office 10 in accordance with the present disclosure. In a preferred embodiment, the central filter 26 is decoupled from the downstream end 54 of the main trunk line 46 and the flexible vacuum lines 38 are decoupled from the at least one branch line 50. The vacuum line cleaning system 60 is then connected to the suction pipe network 18 to create a closed-circuit loop by fluidly connecting the second port 108 of the pump 80 to the downstream end 54 and the filter 84 to the at least one branch line 50 via the filter inlet 112. Cleaning fluid solution 92 is then dispensed into the holding chamber 88 via the chamber inlet 96. The suction pipe network 18 is flushed with cleaning fluid solution 92 by initiating the pump 80, which draws the cleaning fluid solution 92 from the holding chamber 88 and pumps the cleaning fluid solution 92 throughout the suction pipe network 18. Once the cleaning fluid solution 92 reaches the filter 84 via the filter inlet 112, the cleaning fluid solution 92 is filtered to remove any debris or particles suspended in the cleaning fluid solution 92 that is removed from the suction pipe network 18. The filtered cleaning fluid solution 92 is then reintroduced into the holding chamber 88 via the filter outlet 116, where the cleaning fluid solution 92 may be recirculated through the suction pipe network 18. This process may be repeated until the suction pipe network 18 is substantially free of debris. The user may then reverse the pump 80, causing any remaining cleaning fluid solution 92 to be evacuated from the suction pipe network 18. The vacuum line cleaning system 60 is then decoupled from the suction pipe network 18 by disconnecting the pump 80 and filter 84 from the downstream end 54 and the at least one branch line 50, respectively, before the central filter 26 and plurality of flexible vacuum lines 38 are replaced.

As further shown in FIG. 5, if the vacuum line cleaning system 60 further comprises the collection cart 130 having the collection tank 120, then after the cleaning fluid solution 92 has circulated throughout the suction pipe network 18, it may be stored in collection chamber 124 for off-site filtering. Similarly, the cleaning fluid solution 92 may also be filtered by filter 84 before being stored in collection chamber 124. Cleaning fluid solution 92 may also be recirculated after being filtered by filter 84 and stored within collection chamber 124 by being introduced into holding chamber 88 via chamber inlet 96.

Figure 6:
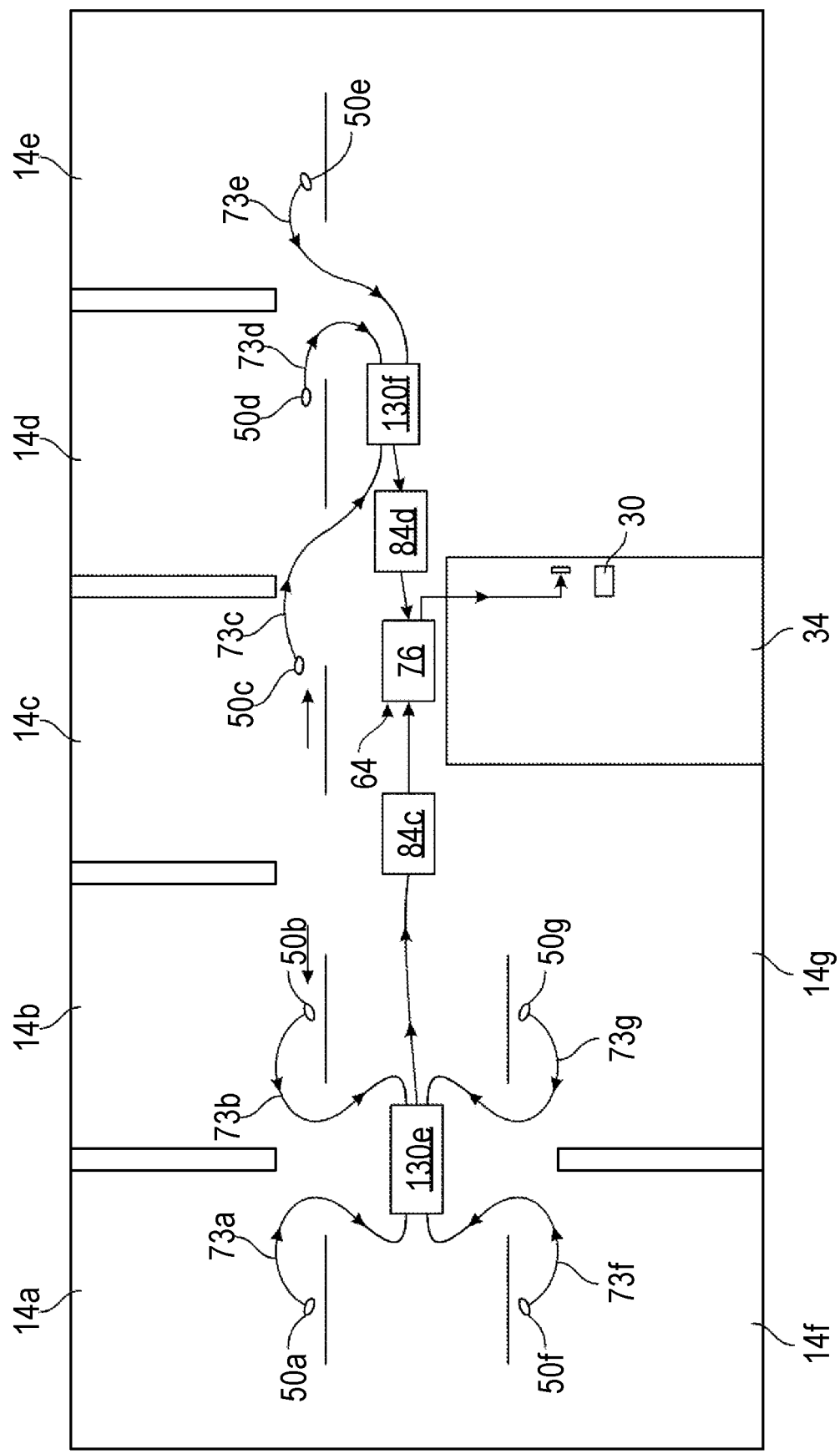
FIG. 6 is an illustration of an exemplary layout of a dental office having an alternative exemplary embodiment of a system for removing debris from a suction pipe network in a dental office.

Referring now to FIG. 6, shown therein is a diagram illustrating a configuration of an exemplary dental office 10 having an alternative exemplary embodiment of the vacuum line cleaning system 60 connected to the suction pipe network 18. As shown in FIG. 6, the dental office 10 has a plurality of examination rooms 14. By way of example, seven examination rooms 14 are shown in FIG. 6 and designated by the reference numerals 14*a*, 14*b*, 14*c*, 14*d*. 14*e*, 14*f*, and 14*g*. The dental office 10, as shown in FIG. 6, is also provided with an equipment room 34 and central suction unit 30. In this embodiment, suction pipe network 18 includes at least one branch line 50. By way of example, seven branch lines 50 are shown in FIG. 6 and designated by the reference numerals 50*a*, 50*b*, 50*c*, 50*d*, 50*e*, 50*f*, and 50*g*. Further, in this embodiment, the vacuum line cleaning system 60 includes at least one filter 84, and at least one collection cart 130. By way of example, two filters and two collection carts 130*e* and 130*f*, each having a collection tank 120*e* and 120*f* are shown to be located in the dental office 10 in FIG. 6. The two filters are designated by reference numerals 84*c* and 84*d*, and the two collection carts are designated by the reference numerals 130*e* and 130*f*. Flexible piping 73 and hoses may be used to fluidly connect the cart 64 having the holding tank 76, the filters 84*c*, 84*d*, and the collection tanks 120*e*, 120*f*. Flexible piping 73 may also be used to fluidly connect the collection tanks 120*e*, 120*f* to branch lines 50*a*-50*g*. By way of example, seven flexible piping 73 are shown in FIG. 6 and designated by the reference numerals 73*a*, 73*b*, 73*c*, 73*d*, 73*e*, 73*f*, and 73*g*. In that embodiment, the collection tanks 120*e*, 120*f* may be in fluid communication with the filters 84*c*, 84*d* such that the cleaning fluid solution 92 may be circulated through the suction pipe network 18 and introduced into the collection chamber 124 of the collection tanks 120*e*, 120*f*, before being transferred to the filters 84*c*, 84*d* to be filtered before being introduced into the holding chamber 88 via the chamber inlet 96 where the cleaning fluid solution 92 may be recirculated.

Figure 8:
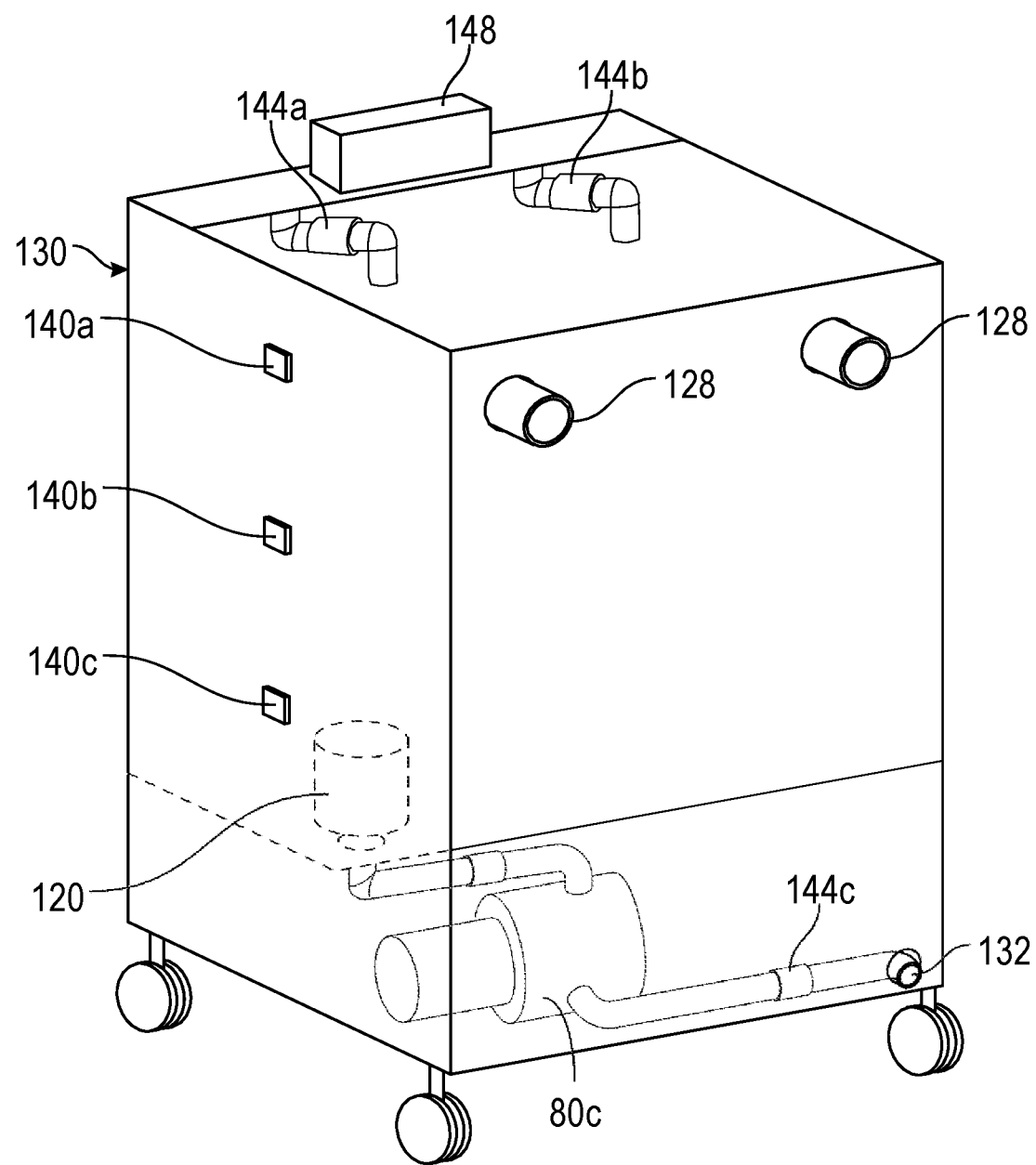
FIG. 8 is a perspective view of an exemplary embodiment of a collection cart of the system for removing debris from the suction pipe network.

In another embodiment, as shown in FIG. 8, the system 60 includes a collection cart 130 supporting the collection tank 120. The collection cart 130 may further include and support one or more fluid sensors 140 to measure the level of fluid within the collection tank 120. By way of example, three fluid sensors 140 are shown in FIG. 8 and designated by the reference numerals 140*a*, 140*b*, and 140*c*. The one or more fluid level sensors 140*a*-140*c* may be positioned within the collection chamber 120. The one or more fluid level sensors 140*a*-140*c* may be, for example, a float sensor.

In that embodiment, the collection cart 130 may further be provided with a collection tank pump 80*c*. The collection tank pump 80*c* may be configured to be fluidly connected to the collection tank 120 via collection chamber outlet 132. The collection tank pump 80*c*, once initiated, may draw circulated cleaning fluid solution 92 from the collection tank 120 via collection chamber outlet 132 and pump the cleaning fluid solution 92 to the holding chamber 88 of the holding tank 76 of the cart 64 via chamber inlet 96.

Figure 7:
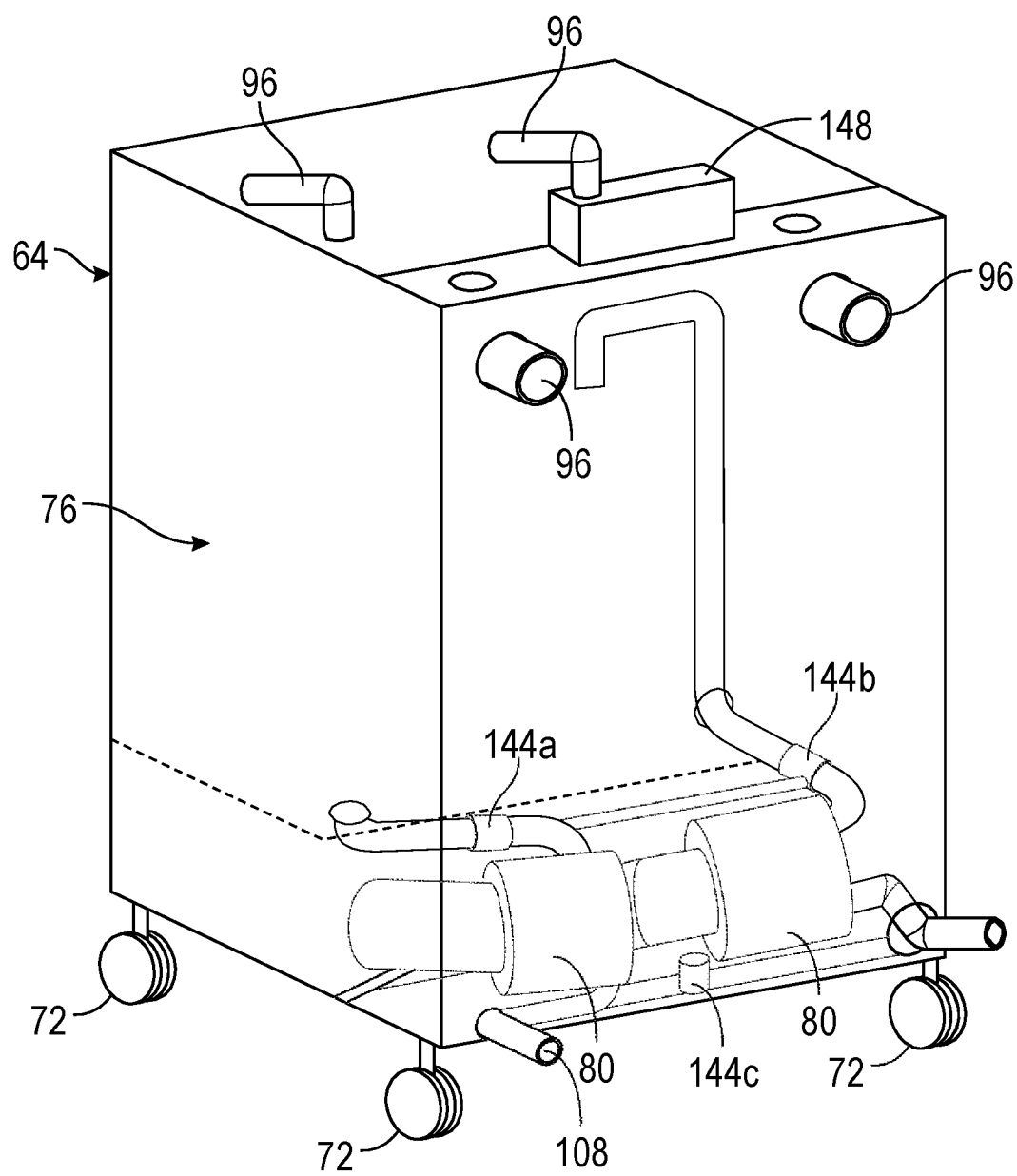
FIG. 7 is a perspective view of an exemplary embodiment of a holding cart of the system for removing debris from the suction pipe network.

In one embodiment, the cart 64 and the collection cart 130 may further be provided with one or more valves 144, as shown in FIGS. 7 and 8, respectively. By way of example, three valves 144 are shown in FIGS. 7 and 8 and are designated by the reference numerals 144*a*, 144*b*, and 144*c*. The one or more valves 144*a*-144*c* may be in fluid communication with first port 104 and the second port 108 to regulate the flow of water and cleaning fluid solution 92 from the pump 80 and the central suction unit 30, as shown in FIG. 7, and in fluid communication with the collection chamber inlet 128 and the collection chamber outlet 132 to regulate flow of fluid to and from the collection chamber 124, as shown in FIG. 8.

In one embodiment, as shown in FIGS. 7 and 8, the vacuum line cleaning system 60 may further include a controller 148 that may activate, deactivate, monitor, and/or control one or more components of the vacuum line cleaning system 60 including, for example, pump 80, the one or more valves 144, and the one or more fluid sensors 140, to affect and control the removal of debris and fluid from the suction pipe network 18. The controller 148 may receive input from a user interface that may be operatively connected to the controller 148 in any manner known in the art. By way of example, the fluid-level measurement data obtained by the one or more fluid level sensors 140 may be transmitted to the controller 148 via any suitable communication network. The controller 148 may perform the operations described above in response to a processor executing software instructions contained in a non-transitory computer-readable medium, such as memory. Additionally, or alternatively, hardwired circuitry may be used in place or in combination with software instructions to implement processes described herein. Circuitry, as used herein, may be analog and/or digital components, or one or more suitably programmed processors (e.g., microprocessors) and associated hardware and software, or hardwired logic. Also, "components" may perform one or more functions. The term "component," may include hardware, such as a processor (e.g., microprocessor), an application specific integrated circuit (ASIC), field programmable gate array (FPGA), a combination of hardware and software, and/or the like. The term "processor" as used herein means a single processor or multiple processors working independently or together to collectively perform a task.

Software may include one or more computer readable instructions that when executed by one or more components cause the component to perform a specified function. It should be understood that the algorithms described herein may be stored on one or more non-transitory computer readable medium. Exemplary non-transitory computer readable mediums may include random access memory, read only memory, flash memory, and/or the like. Such non-transitory computer readable mediums may be electrically based, magnetically based, optically based, and/or the like.

In one embodiment, the controller 148 may be mounted on a surface of the cart 64 and/or the collection cart 130, such as, for example, the exterior surfaces of the holding tank 76 and/or the collection tank 120, as shown in FIGS. 7 and 8, respectively. The controller 148 may be, for example, a touchscreen assembly having a display and circuitry for receiving input from the user interface and controlling the pump 80, the one or more valves 144, and the one or more fluid sensors 140 as described herein.

In another embodiment, removal of debris from the vacuum line in the dental office 10 may include a first phase and a second phase. In the first phase, the central filter 26 is decoupled from the downstream end 54 of the main trunk line 46 and the flexible vacuum lines 38 are decoupled from branch lines 50*a*-50*g*. The vacuum line cleaning system 60 is then connected to the suction pipe network 18 to create a closed-circuit loop by fluidly connecting the second port 108 of the pump 80 to the downstream end 54 and the filter 84 to the branch lines 50*a*-50*g* via the filter inlet 112. The pump 80 is then initiated and maintained at, for example, approximately 40-60 PSI for approximately 5 minutes to detect any obvious leaks. The vacuum line cleaning system 60 is then decoupled from the suction pipe network 18 by disconnecting the pump 80 and filter 84 from the downstream end 54 and the branch lines 50a-50g, respectively, before the central filter 26 and the plurality of flexible vacuum lines 38 are replaced. In the second phase, the vacuum line cleaning system 60 is connected to the suction pipe network 18 as described above and shown in FIG. 6. In this embodiment, each of the collection carts 130 having collection tanks 120e, 120f are provided with one or more valves 144a, 144b, 144c, 144d, 144e, 144f, 144g (not shown) corresponding to each of the one or more examination rooms 14a-g, and the cart 64 is coupled to the suction pipe network 18. The pump 80 is then initiated to circulate cleaning fluid solution 92 through the suction pipe network 18. In one embodiment, the pump 80 is maintained at approximately 40-60 PSI for approximately 5 minutes per valve 144a-144g. It should be noted that cleaning time may vary based on the age and condition of the suction pipe network 18. While cleaning fluid solution 92 is circulated through the suction pipe network 18, as described above, no more than one of the one or more valves 144a-144g corresponding to a particular branch line 50a-g are open at any given time to clean one branch line 50a-g at a time. Once a particular branch line 50a-g is cleaned, the valve associated with the cleaned branch line 50 is closed, and another valve 144 of the valves 144a-g is opened to clean another branch line 50. This process is repeated until all of the branch lines 50a-g have been cleaned. This provides for a constant one-directional fluid flow and to prevents the buildup of significant back pressure. In other words, each of the one or more valves 144a-144g is then opened and closed in a sequential manner throughout the circulation process to separately clean particular ones of the branch lines 50a-g. In one embodiment, the controller 148 may be used to operate the one or more valves 144a-144g in sequence.

From the above description, it is clear that the inventive concept(s) disclosed herein are well adapted to carry out the objects and to attain the advantages mentioned herein, as well as those inherent in the inventive concept(s) disclosed herein. While the embodiments of the inventive concept(s) disclosed herein have been described for purposes of this disclosure, it will be understood that numerous changes may be made and readily suggested to those skilled in the art which are accomplished within the scope and spirit of the inventive concept(s) disclosed herein.

What is claimed is:

1. A method, comprising:
    disconnecting a filter, an amalgam separator and at least one flexible vacuum line from a suction pipe network installed in a medical office, the suction pipe network having a main trunk line, a downstream end, and at least one branch line; and
    passing a neutral pH cleaning fluid solution through the main trunk line from a location downstream of the at least one branch line to flush debris from the main trunk and the at least one branch line.

2. The method of claim 1, further comprising connecting a vacuum line cleaning system to the suction pipe network to form a closed-circuit loop, and wherein passing the neutral pH cleaning fluid solution includes circulating the neutral pH cleaning fluid solution through the closed-circuit loop.

3. A method, comprising:
    decoupling a central vacuum-like unit or an amalgam separator from a suction pipe network installed in a medical office such that the central vacuum-like unit or the amalgam separator is not in communication with the suction pipe network; and
    passing a neutral pH cleaning fluid solution through at least a portion of the suction pipe network installed in the medical office to flush debris from the portion of the suction pipe network.

4. The method of claim 3, further comprising connecting a vacuum line cleaning system to the suction pipe network to form a closed-circuit loop, and wherein passing the neutral pH cleaning fluid solution includes circulating the neutral pH cleaning fluid solution through the closed-circuit loop.

5. The method of claim 3, wherein the portion of the suction pipe network is a first portion of the suction pipe network, and further comprising passing the neutral pH cleaning fluid solution through a second portion of the suction pipe network installed in the medical office to flush debris from the second portion of the suction pipe network.

* * * * *